(12) United States Patent
Sinha

(10) Patent No.: US 6,286,370 B1
(45) Date of Patent: Sep. 11, 2001

(54) METHOD USING ULTRASOUND FOR DETECTING MATERIALS ON METAL SURFACES

(76) Inventor: Naveen Neil Sinha, 112 Shirlane Pl., Los Alamos, NM (US) 87544

(*) Notice: Subject to any disclaimer, the term of this patent is extended or adjusted under 35 U.S.C. 154(b) by 0 days.

(21) Appl. No.: 09/244,245

(22) Filed: Feb. 3, 1999

(51) Int. Cl.$^7$ ................................................. G01N 9/24
(52) U.S. Cl. ............................................... 73/579; 73/622
(58) Field of Search ........................... 73/579, 583, 602, 73/630, 645, 646, 648, 659, 649, 622, 625, 627, 628; 376/249

(56) References Cited

U.S. PATENT DOCUMENTS

| | | | |
|---|---|---|---|
| 4,461,178 | * | 7/1984 | Chamuel ................................. 73/599 |
| 4,539,847 | * | 9/1985 | Paap ....................................... 73/579 |
| 4,604,612 | * | 8/1986 | Watkins et al. ......................... 73/599 |
| 5,092,176 | * | 3/1992 | Buttram et al. ......................... 73/599 |
| 5,095,754 | * | 3/1992 | Hsu et al. ................................ 73/602 |
| 5,456,114 | * | 10/1995 | Liu et al. ................................. 73/597 |
| 5,629,485 | * | 5/1997 | Rose et al. .............................. 73/599 |
| 6,019,000 | * | 2/2000 | Stanke et al. ........................... 73/622 |

\* cited by examiner

*Primary Examiner*—Hezron Williams
*Assistant Examiner*—Rose M. Miller
(74) *Attorney, Agent, or Firm*—Samuel M. Freund

(57) ABSTRACT

A method using ultrasound for detecting the presence of coatings on metal surfaces is described. The characteristics of resonant sound waves established within a metal plate are altered by the acoustic impedance of any coatings present on the surface of the metal in the vicinity of the waves. The amplitude and width of the resonant features are most directly affected and can readily be detected. For example, a reduction of approximately a factor of ten in resonance amplitude has been observed when ice is permitted to coat the surface of the plate. A resonant ultrasound condition is impressed on the plate using a transducer attached thereto on the side of the plate opposite to the coating. A receiving transducer is located next to the resonance inducing transducer. Thus, ice can be detected on the surface of an airplane wing surface using transducers located within the wing's interior. Thin deposits of materials may be detected on the interior surface of a pipe using separated transducers located on the exterior thereof.

5 Claims, 10 Drawing Sheets

METHOD USING ULTRASOUND FOR DETECTING MATERIALS ON METAL SURFACES

FIELD OF THE INVENTION

The present invention relates generally to the detection of deposits on metal surfaces and, more particularly, to the use of ultrasound to detect materials on metal surfaces with specific applications to ice buildup on airplane wing surfaces and solid buildup on the interior of pipes.

BACKGROUND OF THE INVENTION

Ice buildup on airplane wings is one of the aviation industry's most baffling and serious problems. Ice accumulation can reduce the lift of an airfoil in flight, and ice shed during takeoff can damage engine fan blades. Eight major airline accidents, resulting in casualties, since 1982 have been attributed entirely or in part to ice buildup. Early detection of ice can alert the crew to take remedial action before a dangerous situation develops. Several techniques for ice buildup detection currently exist, but most use external sensors that are exposed to the elements where they are subject to damage. See, e.g., "Wing Ice Detector," Lawrence Livermore National Laboratory Technical Production Group Report, October 1995, for a discussion of optical sensing methods; "Deicing-Fluid and Ice-Thickness Monitor For Aircraft," NASA Tech Briefs, page 54, September 1997, for a discussion of vibrating sensing elements; "Wing-Mounted Sensor Warns of Ice Accumulation," by Mark A. Gottschalk, Design News, page 153, Sep. 7, 1992, for a discussion of ionic conduction cells; and "Keeping Ice Off Airplane Wings," by Greg Paula, Mechanical Engineering Magazine, May 1997, for a discussion of electromagnetic sensors.

The petroleum and other chemical industry employ long sections of pipe for transfer of chemicals and for processing. Solid material buildup on the interior of these pipes can eventually block chemical flow within these pipes causing dangerous plant operating conditions or changing process conditions in dynamic reactors. Presently, one determines such blockage from a drop in pressure or a drop in flow rate.

In "Ultrasonic Aircraft Ice Detector Using Flexural Waves," U.S. Pat. No. 4,461,178, which issued to Jacques R. Chamuel, on Jul. 24, 1984, a system for the detection of wing icing by monitoring variations in flexural waves transmitted through the outer plate material of an aircraft airfoil is described. The basis of this approach is that compressional waves are not sensitive to ice accumulation on a metal plate, whereas the flexural modes are sensitive. A pulse is introduced into a metal plate and detected by a receiver at a distance. The pulse generates both compressional wave and flexural waves. Because the compressional waves travel faster than the flexural waves, it is possible to distinguish between the two waves based on arrival times using elaborate gating circuitry and peak detection ratio circuits. The ratio of the amplitude of the compressional wave to that for the flexural wave is thereby determined. This ratio changes with ice accumulation on the plate. The detected signal must be filtered so that aircraft structural vibrations can be removed. Although Chamuel states that the originally generated wave may be in the form of a single pulse, a burst of a preselected frequency, or a continuous wave, there is no teaching as to how to measure the requisite ratio for continuous wave excitation. Moreover, pulsed signals are likely to interfere with aircraft electronics.

In "Ice Detector," U.S. Pat. No. 4,604,612, which issued to Roger D. Watkins et al. on Aug. 5, 1986, a method that uses horizontally polarized Lamb waves to detect the presence of ice on a metal plate is described. A complex arrangement of six strip transducers is employed to generate this particular type of Lamb waves. A tone-burst approach is utilized.

In "Apparatus And Method For Detection Of Icing Onset And Ice Thickness," U.S. Pat. No. 5,095,754, which issued to David K. Hsu et al. on Mar. 17, 1992, it is stated that compressional waves do not adequately distinguish between transmission into ice and transmission into water, and that compressional waves propagating into a water layer and reflected at the water/air interface are practically indistinguishable from the ice/air interface. A buffer block is therefore embedded in the metal in order to delay the echo signal such that the receiver amplifier is not saturated in these pulse-echo measurements.

In "Ultrasonic Method And Apparatus For Detecting And Identifying Contamination Such As Ice On The Surface Of A Structure," U.S. Pat. No. 5,507,183, which issued to Francois Larue and Jerome Bisson on Apr. 16, 1996, an invasive method for detecting deposits on plate structures is described which requires the insertion of a wedge through a hole in the plate. The top surface of the wedge is the actual detecting surface rather than the plate itself. Pulse-echo techniques are employed, and the detection region is localized on the wedge.

Accordingly, it is an object of the present invention to provide a method for detecting ice buildup on airfoils.

Yet another object of the present invention is to provide a method for detecting material buildup on the inside of pipes.

Still another object of the invention is to provide a method for measuring changes in material buildup on metal surfaces.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for detecting materials deposited on metal surfaces hereof may include the steps of: applying sinusoidal vibrational excitation to the metal beneath the surface to be investigated for deposits over a range of frequencies within which a standing-wave pattern is established in the metal; measuring the amplitude and/or the peak width of at least one feature in the standing-wave pattern; and comparing the measured amplitude and/or the measured peak width of the at least one feature in the standing-wave pattern with the amplitude and/or peak width of the corresponding feature in the standing-wave pattern of the uncoated metal, whereby the presence of materials deposited on the metal surface is detected.

Preferably, the wavelength of the sinusoidal vibrational excitation is less than or equal to the thickness of the metal.

In another embodiment of the invention, in accordance with its objects and purposes, as embodied and broadly described herein, the method for detecting materials deposited on metal surfaces hereof, may include the steps of: applying sinusoidal vibrational excitation to the metal beneath the surface to be investigated for deposits having a chosen frequency using a first transducer located on the opposite side of the metal from the deposited material; measuring the amplitude of plate vibrational excitation at a chosen distance from the first transducer using a second transducer located on the same side of the metal as the first transducer; and comparing the measured amplitude with the corresponding amplitude of the uncoated metal, whereby the presence of materials deposited on the metal surface is detected.

Preferably, the wavelength of the sinusoidal vibrational excitation is approximately the thickness of the metal.

Benefits and advantages of the present invention include an inexpensive, rugged, sensitive and reliable method for detecting deposits on metal surfaces such as wings and the interior of pipes, and for determining changes in the thickness of these deposits.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1a is a schematic representation of one embodiment of the apparatus used to demonstrate the method of the present invention showing, in particular, a dual-element concentric transducer attached to the bottom of a metal plate for applying sinusoidal vibrational excitation to the surface of the metal opposite the surface thereof to be investigated for deposits over a range of frequencies within which a standing-wave pattern is established in the metal, and for detecting resonant features in the standing-wave pattern, while FIG. 1b is a schematic representation of an expanded bottom view of the dual-element concentric transducer.

DETAILED DESCRIPTION

Figure 1:
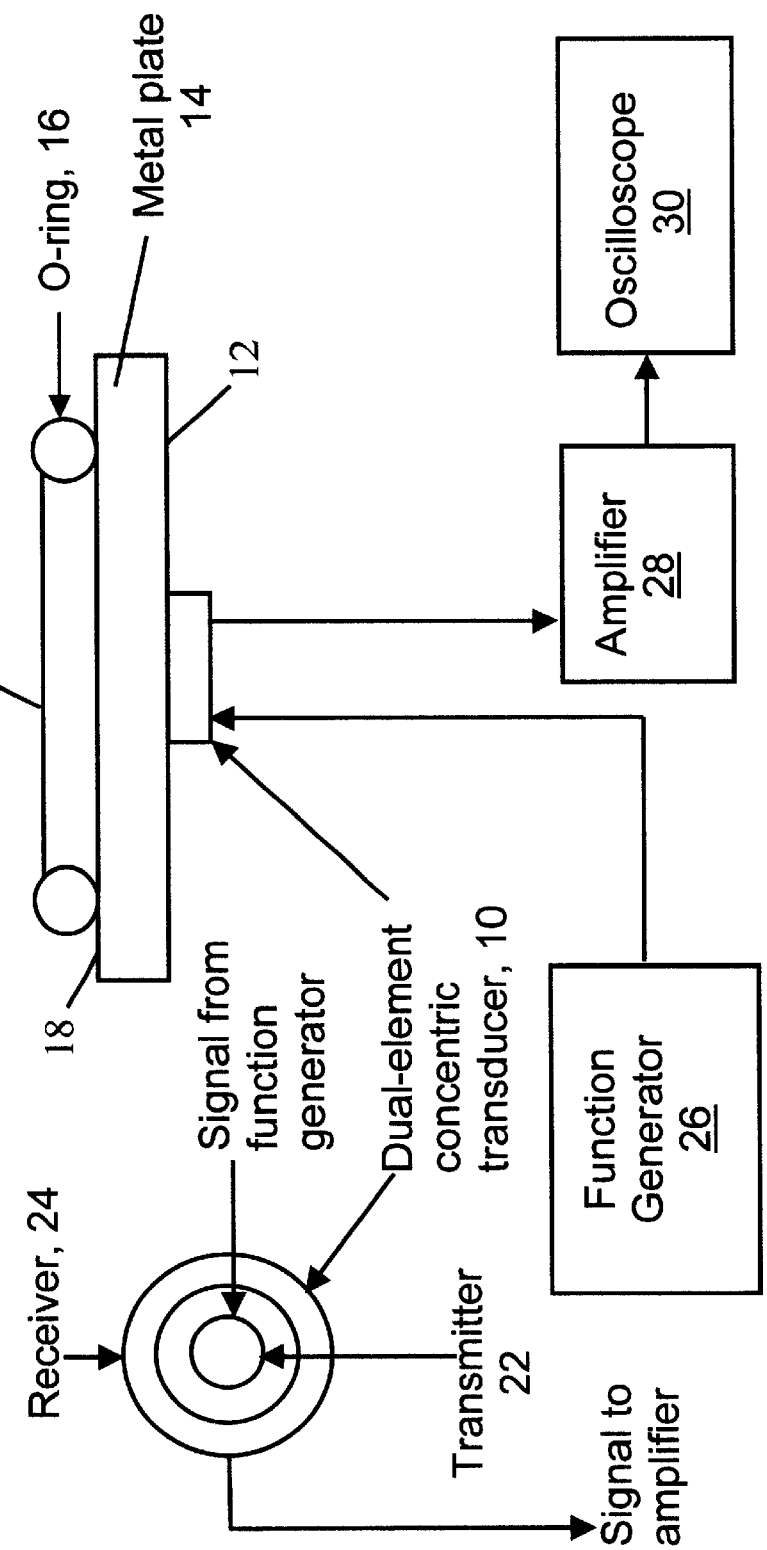

Briefly, the present invention includes the use of ultrasound to detect the presence of deposits on metal surfaces by measuring a change in the metal's thickness mode resonance amplitude and resonance width as a result of the effect of surface deposits on the creation of standing waves inside the metal. This affects the acoustic impedance matching at the surface of the metal and, consequently, the reflection coefficient of the sound waves. Both the introduction of sound waves and the measurement of the amplitude thereof are achieved using transducers on the opposite surface of the metal from that which the deposit is expected. Transducers may be close together if it is desired that absorption of resonant vibrations is to be measured, or spaced-apart at a chosen distance, in which case the absorption of non-resonant plate waves may be measured. This latter measurement increases the sensitivity of the method since a large surface area is interrogated by the method. Typically, the frequency of the sound waves is chosen such that the wavelength thereof is approximately the thickness of the metal under investigation.

A standing wave pattern is established in a resonator cavity formed by the opposite walls of a metal plate using external excitation and its amplitude is detected using a dual-element concentric transducer which both generates sound waves and detects them. Essentially, this device includes two transducers in one package: a transmitter and a receiver. The transmitter transducer converts a sine-wave voltage signal inputs into longitudinal sound waves that propagate through the metal plate, reflect from the opposite wall and can be detected by the receiver transducer as an electric signal. Resonance occurs as a result of sound waves bouncing between the two walls of the plate. When a reflected wave returning to the transmitter is in phase with the new cycle of wave being generated, the two waves interfere constructively to produce a large amplitude, resonant, standing-wave pattern. This in-phase condition occurs at those frequencies for which an integral number of wavelengths fit exactly in the round trip distance from the source to the reflecting surface and back. Thus, a series of equally spaced (in frequency) pronounced resonance peaks, also known as interference peaks, results when the frequency is varied over a wide range. The spacing between any two consecutive interference peaks, $\Delta f_n = f_n - f_{n-1}$, is related to the path length, d (plate wall thickness), and the sound velocity, $c_n$, in the plate at frequency $f_n$ according to $c_n = 2*d*\Delta f_n$. Here, n is the n-th peak. Therefore, each standing wave corresponds to a resonance peak.

As stated hereinabove, the formation of the standing waves depends on reflection from the surface of the plate wall. The reflection coefficient for a metal-air interface is high and essentially all of the signal is reflected back. This permits a clearly developed resonance peak to be observed by the receiver transducer. However, when there is a deposition of some material on the plate surface, the reflection coefficient of the metal-deposition interface changes and a smaller amount of the sound energy is reflected. When there is water on the plate, a certain amount of sound is reflected back and the remainder is transmitted into the water above. Standing waves still develop inside the plate but the reflected wave does not completely cancel the incident wave. This results in a decrease in the resonance peak amplitude and also a broadening of the resonance peak. As the source transducer is introducing sound energy into the plate, some of the energy leaks into the water above which lowers the quality factor (Q) of the resonance. The Q is defined as the ratio of the incident energy and the loss of energy per cycle. More loss, therefore, means lower Q, or a broader resonance peak.

When ice coats the surface of the metal plate, little sound is reflected from the interface and a large fraction is transmitted into the ice layer and is absorbed therein. This dramatically affects the plate resonance. The amplitude is reduced sharply and the peaks broaden significantly. By monitoring both the decrease in amplitude and the increase in peak-width, it is possible to detect the presence of ice or any other deposition on a metal plate. The actual variation depends on the acoustic impedance of the deposit because this is what affects the reflection coefficient from the metal-deposition interface.

Reference will now be made in detail to the present preferred embodiments of the invention examples of which are illustrated in the accompanying drawings. Identical number labels designate similar or identical structure. Turning now to FIG. 1a, a schematic representation of one embodiment of the apparatus used to demonstrate the method of the present invention is shown. Dual element concentric transducer, 10, is placed in contact with surface, 12, of plate, 14. O-ring, 16, is placed on surface, 18, of plate 14 for the purpose of containing chosen heights of liquids or solids, 20, placed in contact with surface 18. Transducer 10 includes a transmitter, 22, for introducing sound waves into plate 14, and a receiver, 24, for detecting sound waves reflected from surface 18, a bottom view thereof being shown schematically in FIG. 1b. Function generator, 26, provides ultrasonic energy to transmitter 22, typically in the range between 1 and 4.5 MHz, because of the bandwidth of the transducer employed, while reflected signals from surface 18 detected receiver 24 are amplified using amplifier, 28, and viewed using oscilloscope, 30. The dual-element concentric transducer attached to the bottom of the metal plate is well suited for applying sinusoidal vibrational excitation to the surface of the metal opposite the surface thereof to be investigated for deposits over a range of frequencies within which a standing-wave pattern is established in the metal, and for detecting resonant features in the standing-wave pattern.

Figure 2:
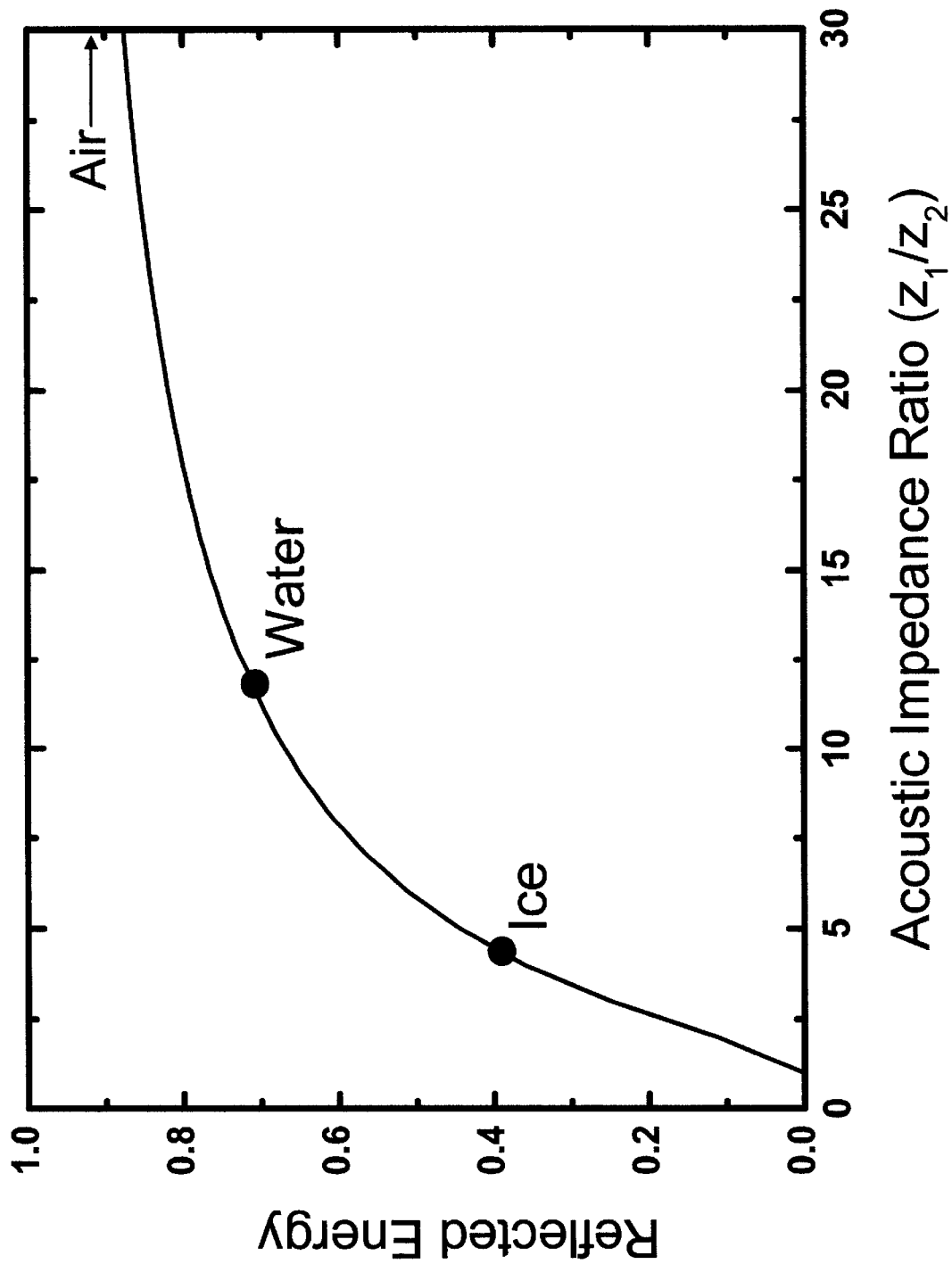
FIG. 2 is a graphic representation of the reflected energy of sound waves from the boundary of an aluminum surface in contact with ice, water or air as a function of the ratios of acoustic impedance of the aluminum to that of ice, water or air respectively.

FIG. 2 is a graphic representation of the reflected energy of sound waves from the boundary of an aluminum surface in contact with ice, water or air as a function of the ratios of acoustic impedance of the aluminum to that of ice, water or air, respectively. Acoustic impedance is a measure of a material's resistance to sound propagation therethrough. The quantity of sound transmitted through or reflected from an interface between two dissimilar materials is proportional to the difference in their acoustic impedances. In FIG. 2, $z_1$ is the acoustic impedance of the deposited material, while $z_2$ represents the acoustic impedance of the metal plate. Thus, if the acoustic impedance of the backing material is much smaller than that of the metal plate, most of the vibrational energy introduced into the plate is reflected at the interface.

Figure 3:
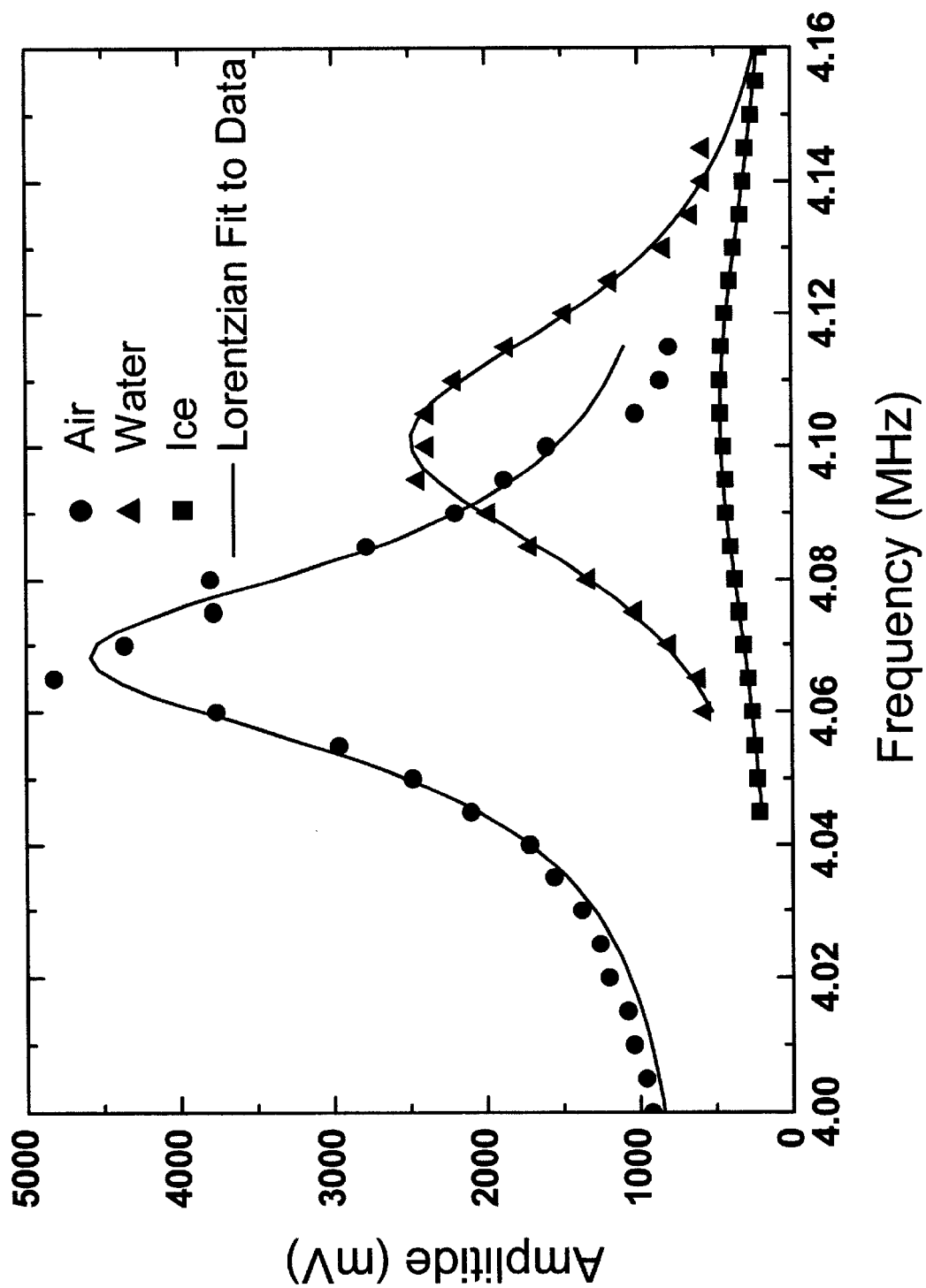
FIG. 3 is a graph of the measured amplitude of the acoustic signal reflected from the surface of a 4.7 mm thick aluminum plate in contact with air, water or ice obtained using the dual-element transducer shown in FIGS. 1a and 1b hereof as a function of sound wave frequency.

FIG. 3 is a graph of the measured amplitude of the acoustic signal reflected from the surface of a 4.7 mm thick aluminum plate in contact with air, water or ice obtained using the dual-element transducer shown in FIGS. 1a and 1b hereof as a function of sound wave frequency as indicated by the solid circles, triangles, and squares, respectively. The solid curves represent Lorentzian fits to the data. It is clear that the expected relationship between acoustic impedance and extent of reflection described in FIG. 2 hereof is demonstrated by the actual measurements. In addition to the peak height of the resonant features decreasing upon changing the exposure of the metal surface to air, water, and ice (4.580 V, 2.486V, and 0.465V, respectively), the width of the features also changes (35.6 kHz, 47.2 kHz, and 94.5 kHz, respectively) in a readily observable manner.

Figure 4:
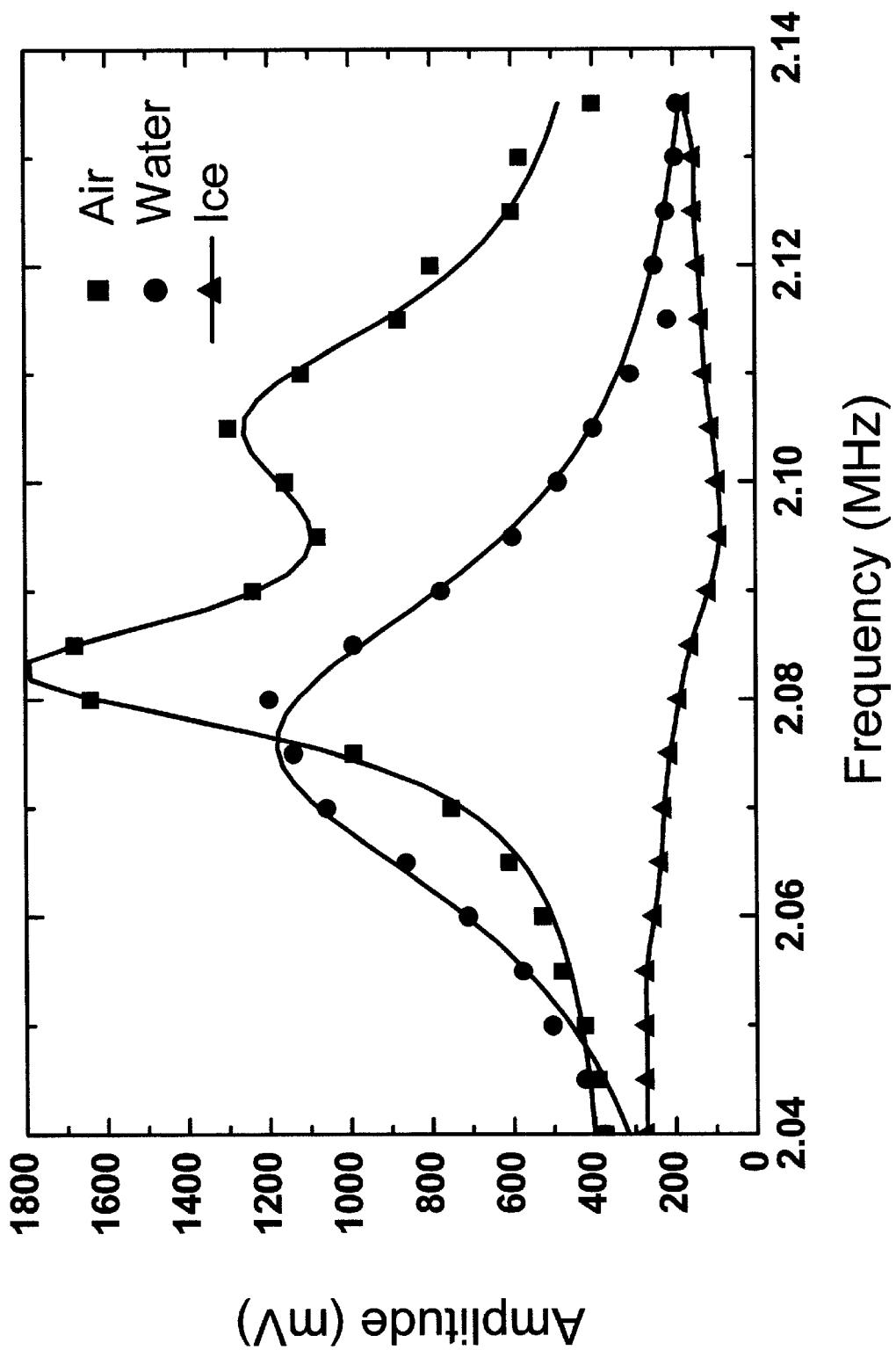
FIG. 4 is a graph of the measured amplitude of the acoustical signal reflected from the surface of a 3.2 mm thick aluminum plate in contact with air, water or ice obtained using the dual-element transducer shown in FIGS. 1a and 1b hereof as a function of sound wave frequency.

FIG. 4 is a graph of the measured amplitude of the acoustical signal reflected from the surface of a 3.2 mm thick aluminum plate in contact with air, water or ice obtained using the dual-element transducer shown in FIGS. 1a and 1b hereof as a function of sound wave frequency as indicated by the solid squares, circles, and triangles, respectively. FIG. 2 is included to demonstrate that the measurements are in general unaffected by the thickness of the metal plate. The shoulder clearly present to higher frequency for the response of the uncoated plated will be described hereinbelow.

Figure 5:
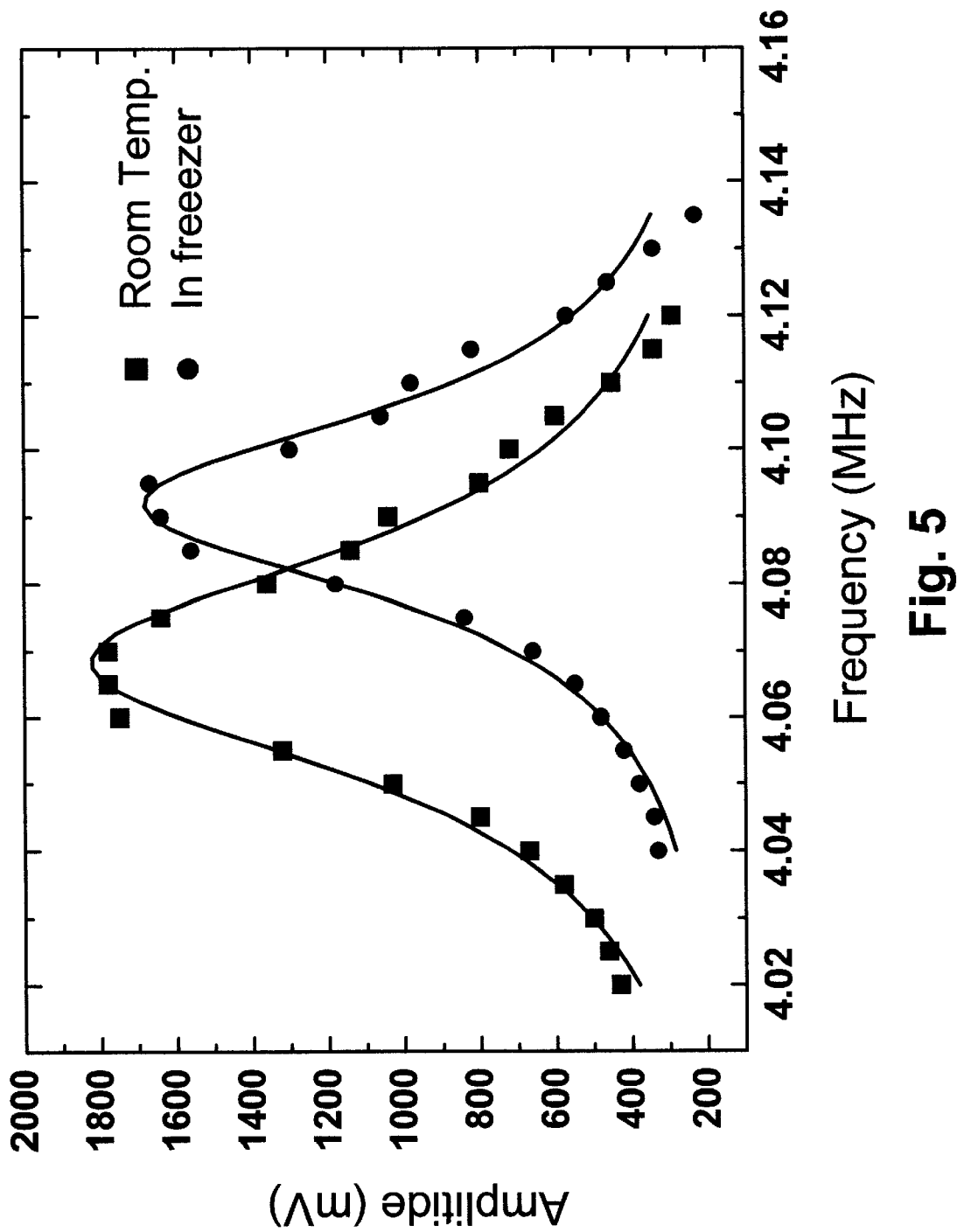
FIG. 5 is a graph of the measured amplitude of the acoustical signal reflected from the surface of a 4.7 mm thick aluminum plate in contact with air at room temperature and at approximately 2° F. using the dual-element transducer shown in FIGS. 1a and 1b hereof.

FIG. 5 is a graph of the measured amplitude of the acoustical signal reflected from the surface of a 4.7 mm thick aluminum plate in contact with air at room temperature and at approximately 2° F., as indicated by the solid square and solid circles, respectively, using the dual-element transducer shown in FIGS. 1a and 1b hereof. Again the solid curves in FIGS. 4 and 5 represent a Lorentzian fit to the data points. This data clearly shows that the temperature variation of the metal plate has little effect on the amplitude of the measurement. The slight shift in the resonant frequency is likely due to a change in tensile properties of the plate.

Figure 6:
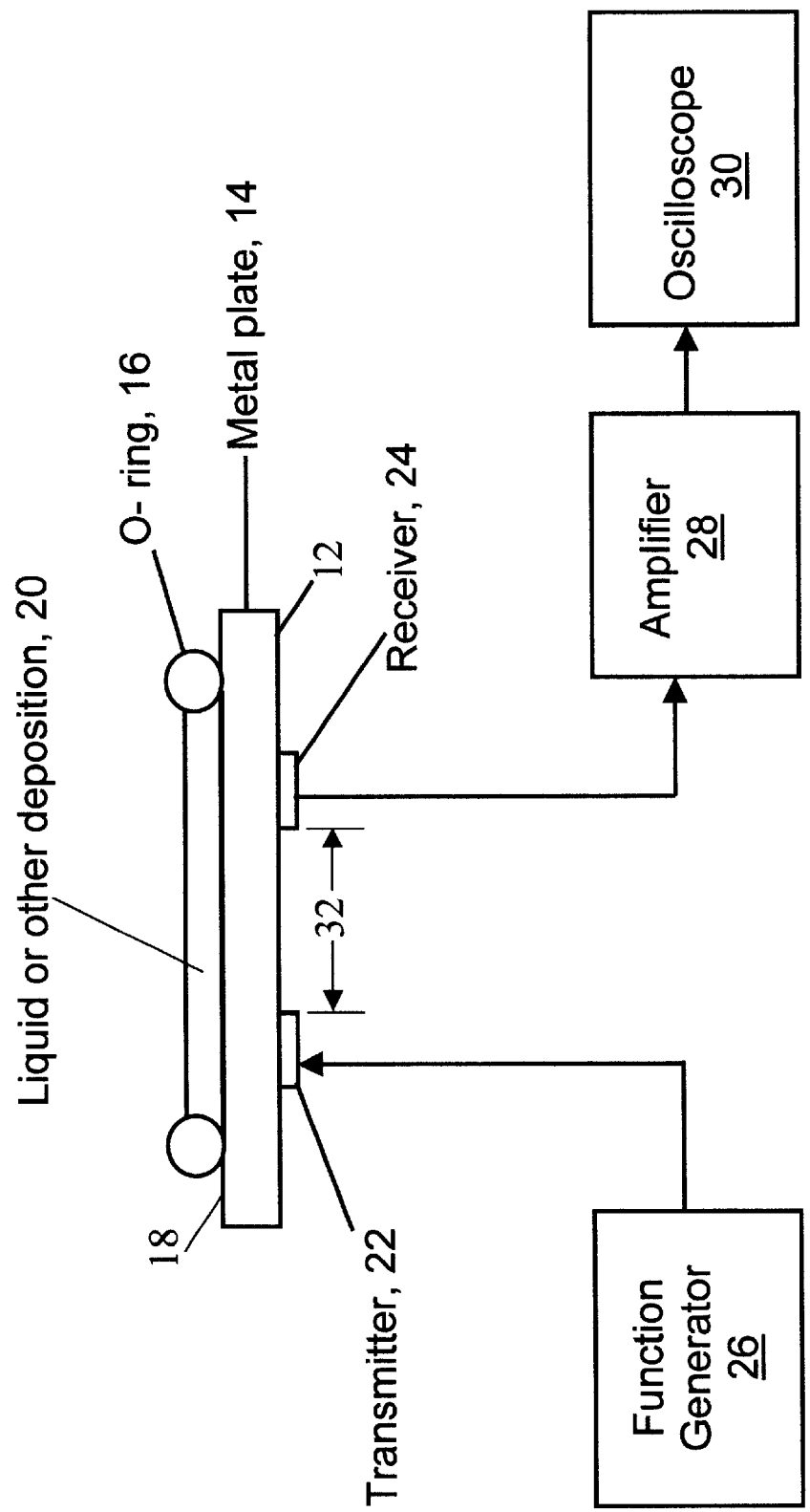
FIG. 6 is a schematic representation of a second embodiment of the apparatus used to demonstrate the method of the present invention showing, in particular, two, spaced-apart transducers attached to the bottom of a metal plate, one for applying sinusoidal vibrational excitation to the metal over a range of frequencies, and the other for detecting the intensity of plate vibrational excitation some distance away from the location of excitation.

FIG. 6 is a schematic representation of a second embodiment of the apparatus used to demonstrate the method of the present invention showing, in particular, two, spaced-apart transducers attached to the bottom of a metal plate, one for applying sinusoidal vibrational excitation to the metal over a range of frequencies, and the other for detecting the intensity of plate vibrational excitation some distance away from the location of excitation. The transducers were typically placed 14 cm apart.

Figure 7:
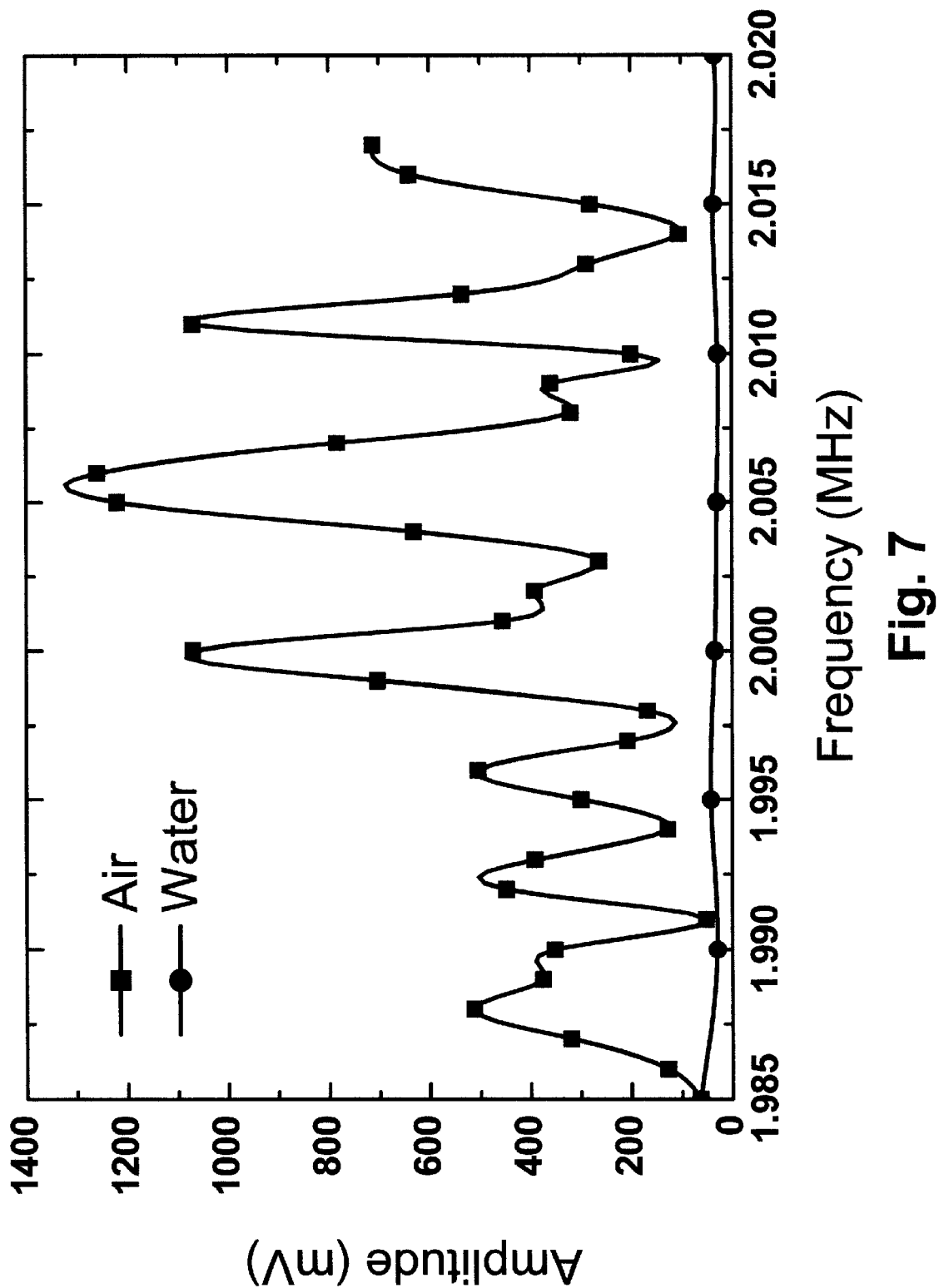
FIG. 7 is a graph showing the amplitude of detected plate waves for a 4.7 mm thick aluminum plate using the apparatus shown in FIG. 6 hereof as a function of applied acoustic wave frequency for air and for water.

FIG. 7 is a graph showing the amplitude of detected plate waves for a 4.7 mm thick aluminum plate using the apparatus shown in FIG. 6 hereof as a function of applied acoustic wave frequency for air and for water, as shown by the solid squares and solid circles, respectively. The presence of ice is expected to have an even stronger effect on amplitude damping.

Figure 8:
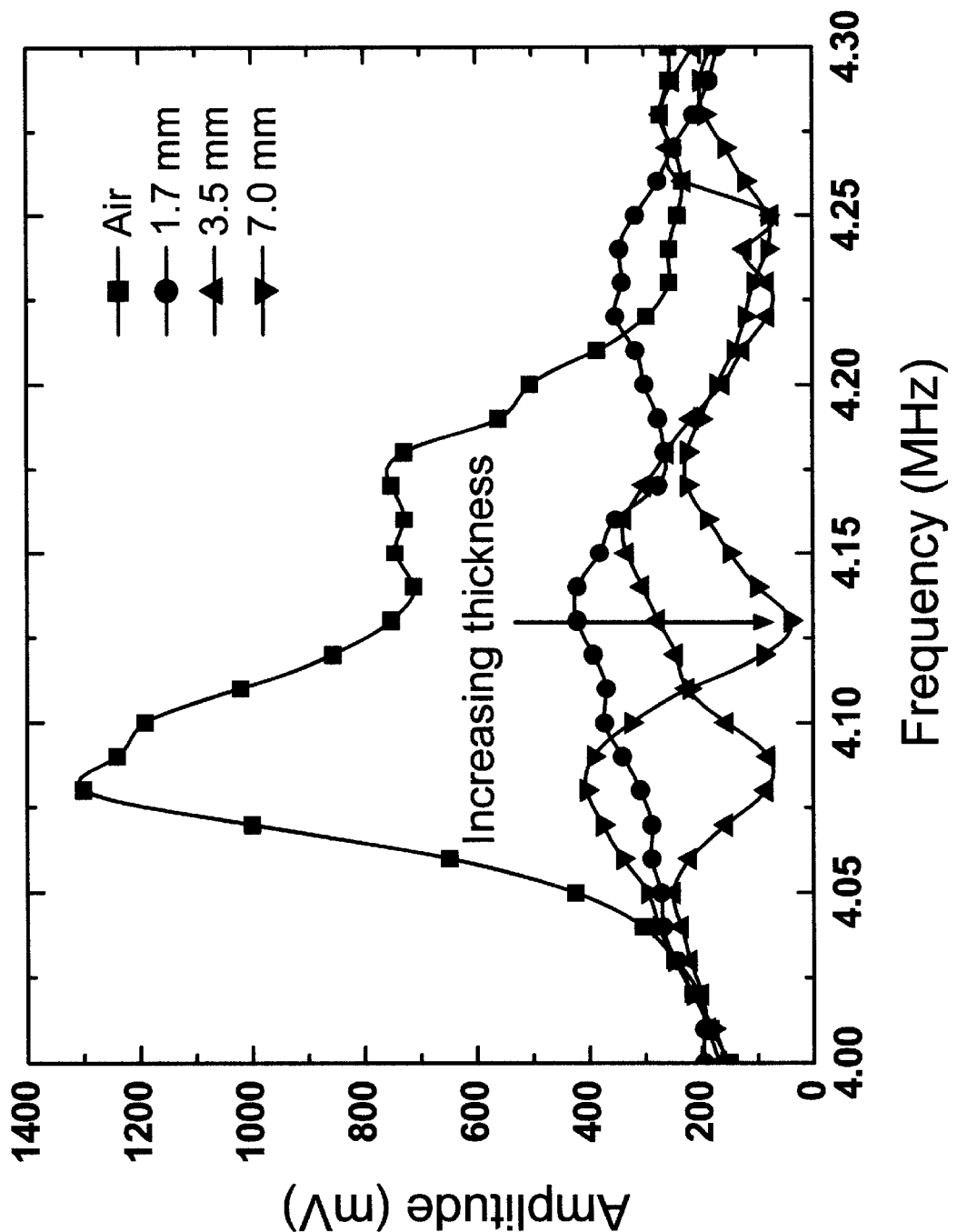
FIG. 8 is a graph showing the amplitude of detected plate waves for a 4.7 mm thick aluminum plate using the apparatus shown in FIGS. 1a and 1b hereof as a function of applied acoustic wave frequency for increasing thicknesses of ice coated thereon.

FIG. 8 is a graph showing the amplitude of detected plate waves for a 4.7 mm thick aluminum plate using the apparatus shown in FIGS. 1a and 1b hereof as a function of applied acoustic wave frequency for increasing thicknesses of ice coated thereon, where the solid squares represent air and the solid circles, triangles and inverted triangles represent 1.7 mm, 3.5 mm and 7.0 mm of ice, respectively. Although curves are multivalued as a function of ice thickness, it is apparent that a frequency may be chosen such that the measured amplitude of the detected sound waves is a monotonic function of ice thickness.

Figure 9:
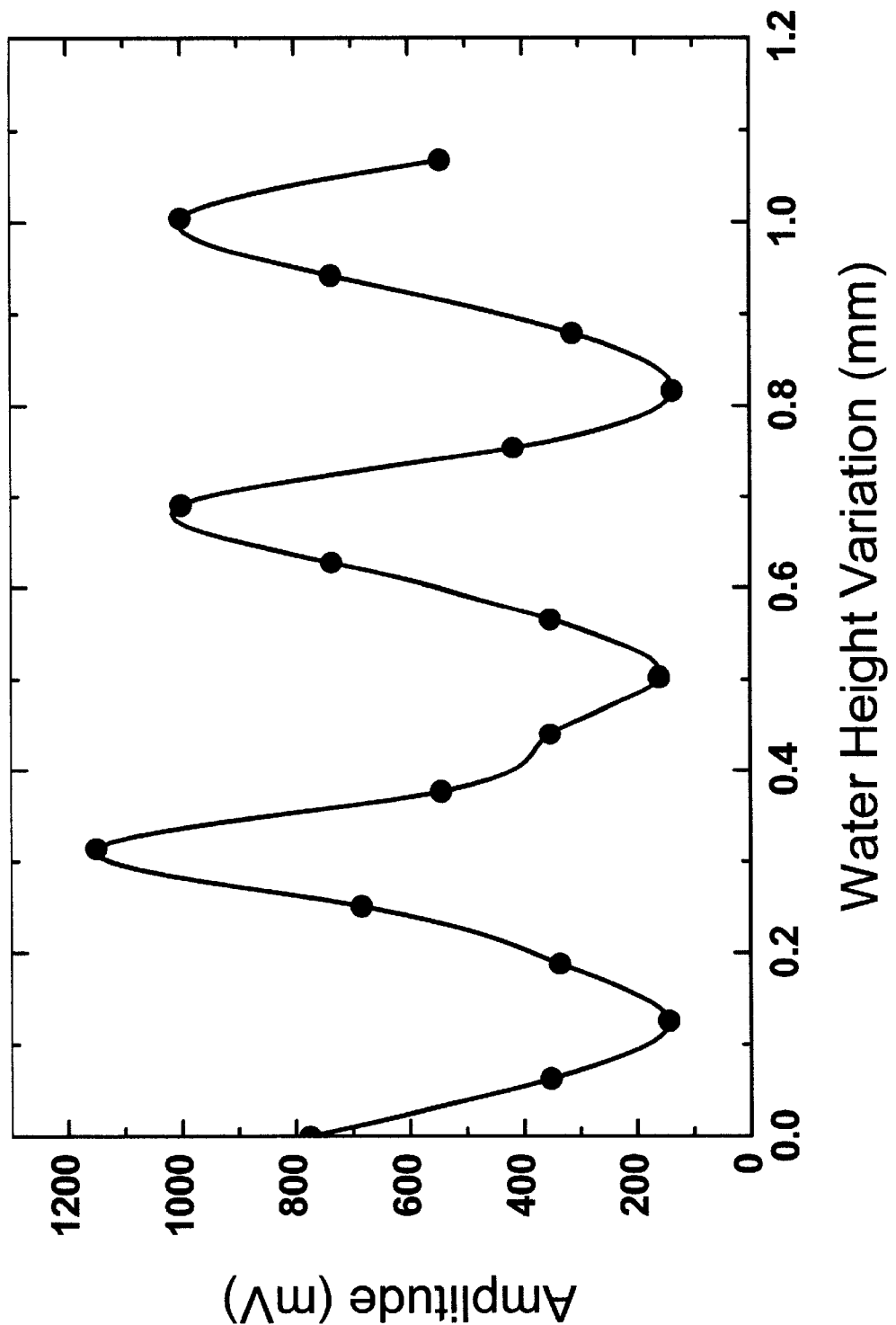
FIG. 9 is a graph showing the amplitude of detected plate waves for a 4.7 mm thick aluminum plate using the apparatus shown in FIGS. 1a and 1b hereof as a function of thickness of water layer deposited on the surface thereof at an applied acoustic wave frequency of approximately 2 MHz.

FIG. 9 is a graph showing the amplitude of detected plate waves for a 4.7 mm thick aluminum plate using the apparatus shown in FIGS. 1a and 1b hereof as a function of thickness of water layer deposited on the surface thereof at an applied acoustic wave frequency of 1.991 MHz. As in FIG. 8 hereof, the absorption curve is multivalued. However, one can readily measure differences in the height of the accumulated water, once a known thickness is used to calibrate the apparatus response. The liquid height resolution is approximately 0.2 $\mu$m with the present simple apparatus.

Figure 10:
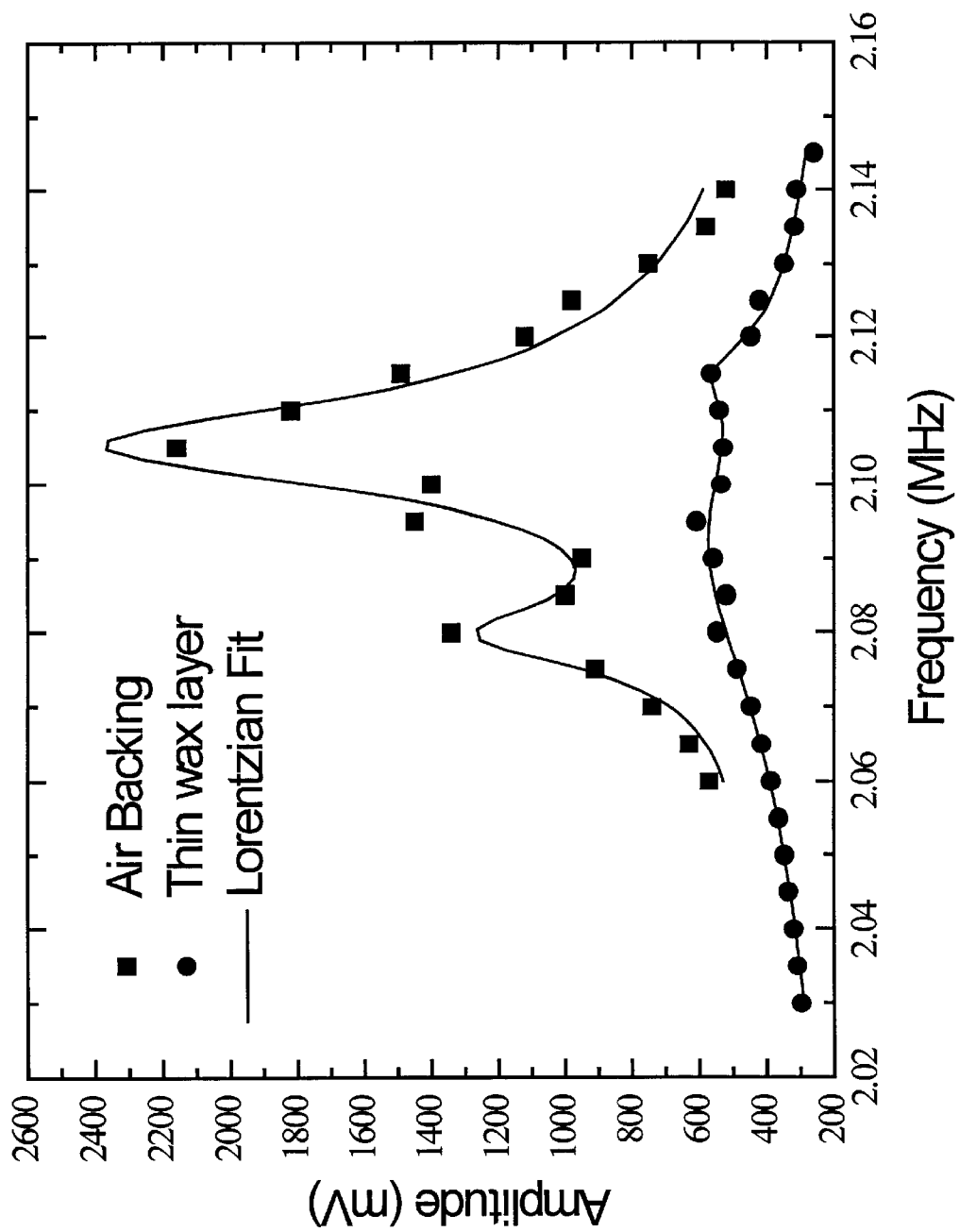
FIG. 10 is a graph showing the amplitude of detected plate waves for a 4.7 mm thick aluminum plate using the apparatus shown in FIGS. 1a and 1b hereof as a function of applied acoustic wave frequency for air and for a wax layer deposited on the surface thereof.

FIG. 10 is a graph showing the amplitude of detected plate waves for a 4.7 mm thick aluminum plate using the apparatus shown in FIGS. 1a and 1b hereof as a function of applied acoustic wave frequency for air and for a candle wax layer approximately 1 mm thick deposited on the surface thereof as is shown by the solid squares and circles, respectively. The solid curves are Lorentzian fits to the data. The additional feature to lower frequencies of the main feature for the metal surface exposed only to air will be described hereinbelow. Once the wax has formed, the measured amplitude is not affected by the presence of fluid in contact with the wax.

Having generally described the present invention, the following discussion provides additional details. If pressure (longitudinal stress) is applied to two opposite sides of a metal cube, thereby squeezing it, the cube will deform in that direction by decreasing its length. At the same time, the cube will bulge at a direction normal to the direction of stress (transverse elongation). The absolute ratio of this transverse deformation to the longitudinal deformation; that is, the relative elongation due to the longitudinal stress, is called Poisson's ratio. This ratio for most metals is close to 0.3 and for aluminum it is 0.355. Therefore, if a longitudinal vibration along its thickness is induced in a metal plate, a vibration in a direction perpendicular to this vibration is also induced due to the Poisson coupling. The actual process is complicated and the waves that are generated along the direction parallel to the surface of the plate are called plate waves. This is a generic term for many types of waves, Lamb waves being one such wave. If the plate is many times thicker than the wavelength of sound induced in that plate, the surface waves are restricted to a very narrow region of the plate surface and decay exponentially into the plate thickness. In other words, these waves propagate only within a thin layer of the plate. However, when the plate thickness is close to the wavelength of sound, the waves that are generated are different. The generated waves now propagate on both sides of the plate. Thus, if a compressional wave transducer is attached to one side of a metal plate, and a frequency of excitation is chosen such that the wavelength of the longitudinal wave generated is similar to the thickness of the plate, it will also generate plate waves that will propagate parallel to the surface on both sides of the plate. FIG. 3 shows the data obtained using the apparatus described in FIG. 1a using a dual-element transducer shown in FIG. 1b. This is a compressional wave transducer. Because of the high frequency used (>1 MHz), the sound beam generated is confined within a very narrow angle above the transducer. The angle ($\alpha$) of beam spreading is given by the equation: sin $\alpha$=1.22c/Df, where, c is the sound speed, f is the frequency of excitation, and D is the diameter of the transducer. The sound will reflect off the opposite surface and spread out slightly. If the thickness of the plate is H, then a receiver transducer placed within distance d where d=H tan $\alpha$ will be within the range of the compressional wave generated by the source transducer. For the dimension of the transducer used for the present demonstration (1-cm diameter of the inner disk-shaped transducer element (callout 22 in FIG. 1a)), the angle of spread for aluminum is approximately 40°. The receiver is a ring element surrounding the source disk, but separated from it by less approximately 1.5 mm (callout 24 in FIG. 1a). Therefore, the receiver will be able to detect the standing waves generated by the longitudinal waves within the thickness of the plate if the plate thickness is more than 2 mm. FIG. 3, shows the thickness mode resonance for a 4.7 mm thick aluminum plate due to standing waves set up by the longitudinal waves generated by the dual-element transducer. As mentioned hereinabove, at the same time the longitudinal waves are generated, plate modes are also generated in the aluminum plate. The plate waves travel along the surface of the plate and reflect at the boundaries of the plate. At certain frequencies, depending on the geometry of the plate, standing waves due to these plate modes are observable. For a dual element transducer, the receiver should detect both the compressional wave resonance within the thickness of the plate and also the resonances due to the plate waves within the boundaries of the plate. However, since the thickness mode resonance signal is much stronger than the plate wave resonance as detected by the ring transducer this signal is not easily observed. For the air-backed (highest amplitude) resonance data shown in FIG. 3, plate wave resonances may be observed to the high frequency side of the peak. The Lorenztian curve fit simply ignores these resonances and fits the thickness mode resonance only.

FIG. 4 shows data for a thinner aluminum plate (3.2 mm). Here, the presence of the plate wave resonances are more readily apparent. The second peak to the high frequency side of the large peak is due plate waves. The effect is even more pronounced for the data shown in FIG. 8 hereof.

If the transmitter (source) and the receiver transducers are separated more than 2–3 times the thickness of the plate, then the receiver will detect very little of the compressional waves generated by the source transducer. Where the transducers are physically separated (FIGS. 6 and 7 hereof), the receiver transducer will detect predominantly the generated plate-wave resonances. The peak spacing between consecutive resonances will depend on the size of the plate: larger dimensions yield smaller peak spacings. As shown in FIG. 7, these waves are strongly damped by the presence of any deposition (water in this case). The maximum distance the two transducers can be set apart for this type of measurement depends on the excitation signal level, the thickness of the plate, and the material of the plate. It is not necessary to generate resonances within the physical boundaries of the plate. The propagated wave from the transmitter to the receiver can alternatively be observed. When deposits are present, the received signal amplitude will be damped thereby. In the present demonstration, only a finite size plate was used which allowed the plate-wave resonances to be clearly observed. FIG. 9 shows how the thickness of a liquid layer on the surface of a metal plate can be measured with high resolution using transducers located on the opposite side of the plate from the deposit. Monitoring of small changes in the liquid level in sealed tanks or other containers can be noninvasively achieved. In the present example, a single excitation frequency that corresponds to one of the thickness mode resonances of the plate was chosen. Whenever, the liquid height becomes an integral number of half-wavelengths of sound in the liquid, a standing wave is produced and a peak in the amplitude of the sine-wave is detected. FIG. 9 hereof shows a series of such resonance peaks. The spacing of these peaks depends on the excitation frequency used; higher frequencies result in smaller spacings.

For high-resolution monitoring of liquid layers for feedback control of liquid layer thickness, the change in amplitude at a frequency corresponding to a side of the resonance peak is monitored. For the example shown if FIG. 9, the amplitude varies by 1000 mV for a variation of 0.2 mm in liquid height. Since signal amplitudes can readily be measured within 1 mV, changes in liquid thickness of 0.2 $\mu$m may be determined. This is smaller than the wavelength of red light of 0.63 micrometer. The present measurement was performed at a frequency of approximately 2 MHz. Using twice (or higher) the frequency would double the resolution.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for detecting materials on metal surfaces, which comprises the steps of:
   (a) applying sinusoidal vibrational excitation normal to the surface of the metal opposite the surface thereof to be investigated for deposits over a range of frequencies such that the wavelength of the sound waves induced in the metal is less than the thickness of the metal, and within which a standing-wave pattern is established;
   (b) measuring the amplitude and/or the peak width of at least one feature in the standing-wave pattern in approximately the region wherein the sinusoidal vibrational excitation is applied to the metal surface; and
   (c) comparing the measured amplitude and/or the measured peak width of the at least one feature in the standing-wave pattern with the amplitude and/or peak width of the corresponding feature in the standing-wave pattern of the uncoated metal, whereby the presence of materials on the metal surface is detected.

2. The method for detecting materials on metal surfaces as described in claim 1, wherein the range of operation of the transducers is between 1 and 4.5 MHz.

3. The method for detecting materials deposited on metal surfaces as described in claim 1, wherein the material is water or ice and the metal surface is an airplane wing.

4. A method for detecting the deposition of ice on the surface of an airplane wing, which comprises the steps of:
   (a) applying sinusoidal vibrational excitation normal to the metal surface of the wing opposite the surface thereof to be investigated for ice deposit over a range of frequencies such that the wavelength of the sound waves induced in the metal wing surface is less than the thickness of the metal of the wing, and within which a standing-wave pattern is established;
   (b) measuring the amplitude and/or the peak width of at least one feature in the standing-wave pattern in the region wherein the sinusoidal vibrational excitation is applied to the metal wing surface; and
   (c) comparing the measured amplitude and/or the measured peak width of the at least one feature in the standing-wave pattern with the amplitude and/or the peak width of the corresponding feature in the standing-wave pattern of the uncoated metal wing surface, whereby the presence of ice on the metal wing surface is detected.

5. A method for determining the thickness of materials on the inside surface of a metal pipe, which comprises the steps of:
   (a) applying sinusoidal vibrational excitation having a chosen frequency normal to the outside surface of the metal pipe using a first transducer, such that the wavelength of sound waves induced in the metal pipe is less than the thickness of the metal and within which a standing-wave pattern is established;
   (b) measuring the amplitude of vibrational excitation in the vicinity of the first transducer using a second transducer located on the outside surface of the metal pipe as the first transducer; and
   (c) comparing the measured amplitude with the corresponding amplitude of the uncoated metal pipe, whereby the presence of materials on the inside surface of the metal pipe is determined.

* * * * *